(12) United States Patent
Lee et al.

(10) Patent No.: US 6,943,022 B2
(45) Date of Patent: Sep. 13, 2005

(54) INHIBITION OF APOPTOSIS BY THE EXPRESSION OF ANTISENSE RNA OF CASPASE-3

(75) Inventors: Gyun Min Lee, Daejon (KR); No Soo Kim, Daejon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 366 days.

(21) Appl. No.: 10/245,813

(22) Filed: Sep. 17, 2002

(65) Prior Publication Data

US 2003/0060443 A1 Mar. 27, 2003

(30) Foreign Application Priority Data

Sep. 17, 2001 (KR) .................................... 2001-0057353

(51) Int. Cl.⁷ ............................. C12N 5/00; C07H 21/04
(52) U.S. Cl. ...................... 435/375; 435/320.1; 435/6; 536/24.5
(58) Field of Search .................... 435/375, 6, 320.1, 435/455; 536/24.5, 23.1; 514/44

(56) References Cited

U.S. PATENT DOCUMENTS

| | | | |
|---|---|---|---|
| 6,303,374 B1 | 10/2001 | Zhang et al. | |
| 2002/0001806 A1 * | 1/2002 | Huang et al. ................. | 435/6 |

OTHER PUBLICATIONS

U. Galderisi et al., "Antisense Oligonucleotides as Therapeutic Agents," Jounral of Cellular Physiology, 181:251–257, 1999.

S.L. McKenna et al., "Inhibition of Caspase Activity Delays Apoptosis in a Transfected NS/0 Myeloma Cell Line," Biotechnology and Bioengineering, 67(2):165–176, Jan. 20, 2000.

* cited by examiner

Primary Examiner—Sean McGarry
Assistant Examiner—Jon B. Ashen
(74) Attorney, Agent, or Firm—Gates & Cooper LLP

(57) ABSTRACT

The present invention relates to an antisense nucleotide of caspase-3, an expression vector encoding antisense RNA of caspase-3, and an inhibition method of cellular apoptosis in recombinant Chinese hamster ovary (CHO) cells using the same. More precisely, the present invention relates to an antisense nucleotide composed of a base sequence represented by Sequence ID No. 1, which suppresses the expression of caspase-3, an expression vector containing the above antisense nucleotide and expressing antisense RNA of caspase-3, and an inhibition method of apoptosis of recombinant cells by suppressing the expression of caspase-3 through introducing the above expression vector into the recombinant cells and then expressing antisense RNA of caspase-3. According to the present invention, apoptosis can be inhibited by suppressing the activation of caspase-3, which is related to the apoptosis, and the integrity of target protein produced in the recombinant cells can be enhanced.

6 Claims, 7 Drawing Sheets

SEQUENCE LISTING

<160> NUMBER OF SEQ ID NOS: 5

<210> SEQ ID NO 1
<211> LENGTH: 200
<212> TYPE: DNA
<213> ORGANISM: Artificial Sequence
<220> FEATURE:
<223> OTHER INFORMATION: Antisense nucleotide to caspase-3

<400> SEQUENCE: 1

```
gtaccagacc gtgatgtcat tccagtgctt ttatgaaaat tcttattatt aactattata      60
cataaaccca tctcaggata atccatttta taactgttgt ccagggatat tccagagtcc     120
attgattcgt ttccatgtat gatctttggt tccaaatttt taatggattt tgaatccact     180
gagttttcag tgttctccat                                                 200
```

<210> SEQ ID NO 2
<211> LENGTH: 24
<212> TYPE: DNA
<213> ORGANISM: Artificial Sequence
<220> FEATURE:
<223> OTHER INFORMATION: casp3L primer

<400> SEQUENCE: 2

```
gctctagaat ggagaacact gaaa                                             24
```

<210> SEQ ID NO 3
<211> LENGTH: 24
<212> TYPE: DNA
<213> ORGANISM: Artificial Sequence
<220> FEATURE:
<223> OTHER INFORMATION: casp3R primer

<400> SEQUENCE: 3

```
cgggatcctt agtgataaaa atag                                             24
```

<210> SEQ ID NO 4
<211> LENGTH: 21
<212> TYPE: DNA
<213> ORGANISM: Artificial Sequence
<220> FEATURE:
<223> OTHER INFORMATION: casp3R200 primer

<400> SEQUENCE: 4

```
cggaatccgt accagaccgt g                                                21
```

```
<210> SEQ ID NO 5
<211> LENGTH: 24
<212> TYPE: DNA
<213> ORGANISM: Artificial Sequence
<220> FEATURE:
<223> OTHER INFORMATION: casp3L200 primer

<400> SEQUENCE: 5
gctctagagc tcctggttca tcca                                              24
```

INHIBITION OF APOPTOSIS BY THE EXPRESSION OF ANTISENSE RNA OF CASPASE-3

FIELD OF THE INVENTION

The present invention relates to an antisense nucleotide of caspase-3, an expression vector encoding antisense RNA of caspase-3, and an inhibition method of cellular apoptosis in recombinant Chinese hamster ovary (CHO) cells using the same. More precisely, the present invention relates to an antisense nucleotide composed of a base sequence represented by Sequence ID No. 1, which suppresses the expression of caspase-3, an expression vector containing the above antisense nucleotide and expressing antisense RNA of caspase-3, and an inhibition method of apoptosis of recombinant cells by suppressing the expression of caspase-3 through introducing the above expression vector into the recombinant cells and then expressing antisense RNA of caspase-3. According to the present invention, apoptosis can be inhibited by suppressing the activation of caspase-3, which is related to the apoptosis, and the integrity of target protein produced in the recombinant cells can be enhanced.

BACKGROUND OF THE INVENTION

The CHO cell line has been widely used for the production of target proteins such as recombinant antibody, human interferon-gamma (Goldman, et al., 1997, *Cytotechnology*, 23, 103–111), factor VIII (Ganne and Mignot, 1991, *Cytotechnology*, 6, 233–40), and thrombopoietin (Kim, et al., 2000, *Biotechnol. Prog.*, 16, 775–781). For the production of target proteins in recombinant CHO cell cultures, production speed rate indicated the amounts of produced proteins per time unit from the live cells is important. In order to enhance the production speed rate, sodium butyrate (NaBu), which is known to enhance productivity by inducing transcription of foreign gene, has been used (Palermo, et al., 1991, *J. Biotechnol.*, 19, 35–47). Despite the positive effect of sodium butyrate on protein production, there is a limitation in its application at a relatively high concentration to recombinant CHO cell culture for foreign protein production, since sodium butyrate can also inhibit cell growth, followed by rapid induction of apoptotic cell death of CHO cells. To fully exploit the beneficial effect of sodium butyrate on foreign protein production, a strategy of overcoming its cytotoxic effect has been attempted by the overexpression of survival proteins like Bcl-2 in CHO cells (Tey, et al., 2000, *Biotechnol. Bioeng.*, 68, 31–43). Overexpression of Bcl-2 extended the culture longevity of recombinant CHO cells during batch culture by suppressing the NaBu-induced apoptosis and thereby resulted in doubling the final antibody concentration (Kim and Lee, 2000, *Biotechnol. Bioeng.*, 71, 184–193). Although the overexpression of survival protein can endow the cells with more robustness in various culture modes and sub-optimal culture conditions (Cotter and Al-Rubeai, 1995, *TIBTECH*, 13, 150–155), most survival proteins have oncogenic properties. The oncogenic property may give rise to regulatory problems in the commercial production of therapeutic proteins. Thus, it may be necessary to screen potent apoptosis inhibitors other than survival proteins.

The cellular pathway leading to apoptosis involves the activation of members of a family of protease, caspases. To date, fourteen members of the caspase family have been identified in vertebrates, and at least eight are known to be involved in apoptotic cell death (Saunders, et al., 2000, *Anal. Biochem.*, 284, 114–124). Among the various apoptosis-related caspases, extensive research has been performed on caspase-3, because caspase-3 has a broad range of intracellular protein substrates (Han, et al., 1997, *J. Biol. Chem.*, 272, 13432–13436). Previously, the present inventors demonstrated that significant elevation in caspase-3 activity preceded the apparent physiological apoptotic progress induced by sodium butyrate and that the overexpression of Bcl-2 inhibited the NaBu-induced apoptosis by suppressing the activation of caspase-3 (Kim and Lee, 2000, *Biotechnol. Bioeng.*, 71, 184–193). There are some reports that apoptosis is blocked successfully in NS0 and CHO cells by inhibiting the activity of caspase-3 or caspase-3-like proteases. At this time, peptide caspase inhibitor (McKenna and Cotter, 2000, *Biotechnol. Bioeng.*, 67, 165–176) or metal cadmium (Yuan, et al., 2000, *Toxicol. Appl. Pharmacol.*, 164, 321–329) is used to inhibit the caspase-3 activity. The use of peptide and metallic inhibitors of apoptosis, however, is unfavorable in large-scale commercial production of recombinant protein because of the high cost of peptide inhibitor and the carcinogenic properties of metallic inhibitor.

The antisense technology may be an alternative to suppress NaBu-induced apoptosis in recombinant CHO cells. Antisense strategy can be performed as transcription of antisense full sequence or partial fragment of target gene, or as introduction of an exogenous antisense oligonucleotide. Despite the time-consuming, laborious process in specific gene knockout, the transcription of antisense sequence is preferred to the introduction of exogenous antisense oligonucleotides because of its efficiency and low cost (Prati, et al., 1998, Biotechnol. *Bioeng.*, 59, 445–450). Furthermore, although depending on both the sense and antisense sequences, the expression of antisense RNA of caspase seems to be able to achieve complete inhibition of apoptotic cell death at a low level of expression of antisense RNA, removing the negative effect on growth rate and productivity originated from the synthesis of large quantities of survival protein (Singh, et al., 1997, *Cytotechnology*, 23, 87–93).

Thus, the present inventors adopted the antisense technology to suppress the NaBu-induced apoptosis. The present invention has been accomplished by confirming that apoptosis caused by sodium butyrate is suppressed when the expression vector inducing antisense RNA transcription for caspase-3 is introduced to the recombinant CHO cells producing a humanized antibody specific to S-surface antigen of hepatitis B virus.

SUMMARY OF THE INVENTION

It is an object of the present invention to provide an antisense nucleotide of caspase-3, which is related to cellular apoptosis, an expression vector encoding antisense RNA of caspase-3, and an inhibition method of cellular apoptosis in recombinant CHO cells using the same.

BRIEF DESCRIPTION OF THE DRAWINGS

The application of the preferred embodiments of the present invention is best understood with reference to the accompanying drawings, wherein.

DETAILED DESCRIPTION OF PREFERRED EMBODIMENTS

Figure 1:
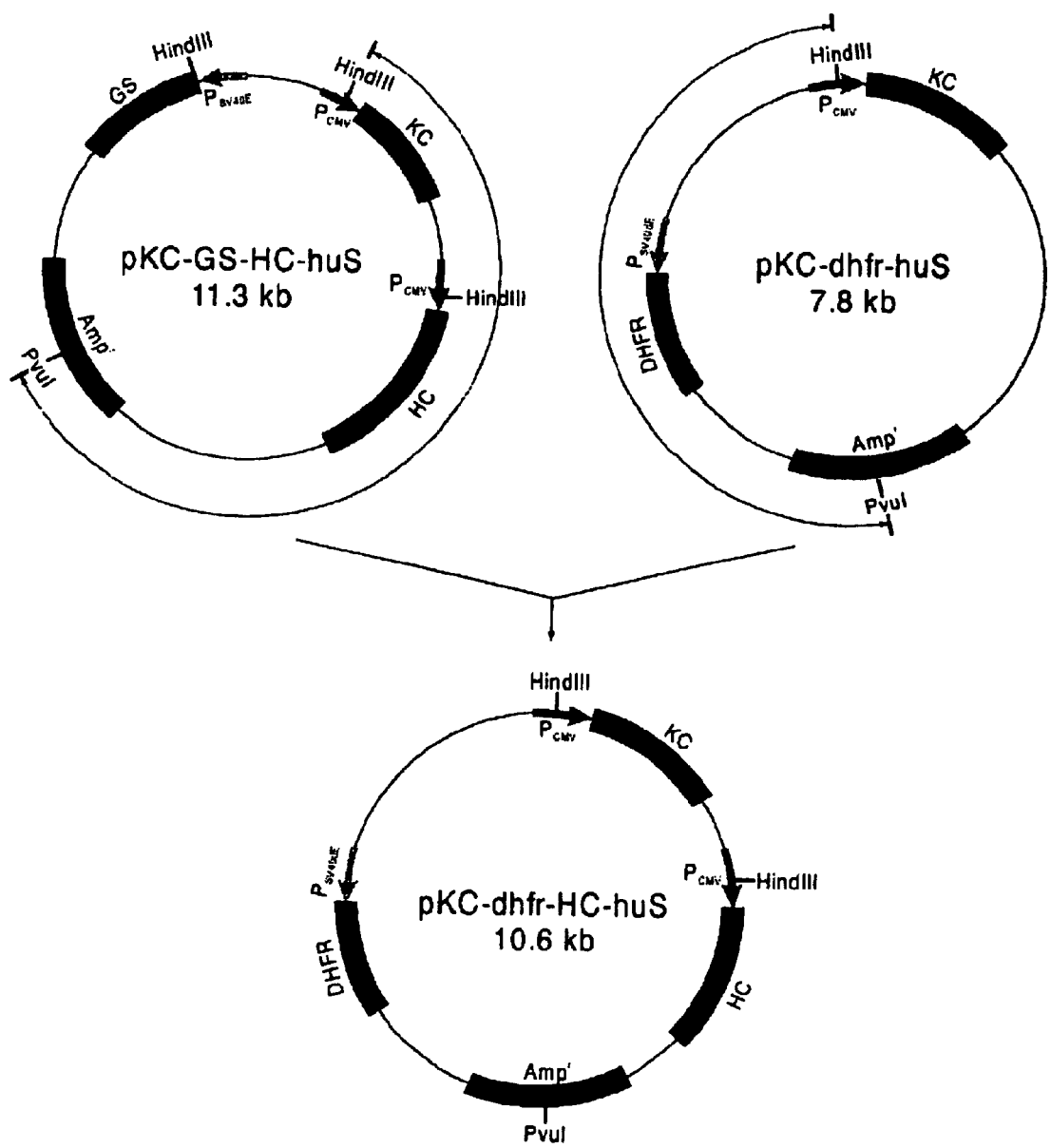
FIG. 1 is a schematic diagram showing the structure of an expression vector designed to express light and heavy chains of humanized antibody specific to the S-surface antigen of hepatitis B virus in CHO cells.

The present invention provides an antisense nucleotide composed of base sequence represented by SEQ. ID No. 1 which is suppressing the expression of caspase-3, an expression vector containing the above antisense nucleotide and expressing antisense RNA of caspase-3, and an inhibition method of apoptosis of recombinant cells by suppressing the expression of caspase-3 through introducing the above expression vector into the recombinant cells and then expressing antisense RNA of caspase-3.

Hereinafter, the present invention is described in detail.

The expression vector ASCASP3-200 containing the antisense nucleotide of caspase-3 represented by the SEQ. ID No. 1 suppressing the expression of caspase-3 of the present invention was constructed as follows. The cDNA pool was prepared from mRNAs of CHO cells by reverse transcription polymerase chain reaction. The caspase-3 cDNA fragment was amplified from cDNA templates by polymerase chain reaction using two primers (i.e., casp3L and casp3R) containing the start codon and stop codon of caspase-3 gene. The primer sequences were derived from caspase-3 sequence of human Jurkat T-lymphocytes (Fernandes-Alnemri, et al., 1994, *J. Biol. Chem.*, 269, 30761–30764). The full-length caspase-3 cDNA fragment was inserted into the multi-cloning site of pBluescript II SK(−) cloning vector (manufactured by Stratagene of La Jolla, Calif.), yielding pBlue-casp3. The partial fragment containing 5' 200 bp of caspase-3 cDNA was amplified using two primers (i.e., casp3L and casp3R200) containing the stop codon and caspase-3 cDNA internal region, which is approximately 200 bp apart from the 5' start codon. The amplified partial fragment of caspase-3 cDNA was inserted, in inverted orientation, into the multi-cloning site of pcDNA3.1-zeo (manufactured by InVitrogen of Carlsbad, Calif.), yielding ASCASP3-200.

The present inventors have deposited the above expression vector, ASCASP3-200, at Korean Collection for Type Cultures, Korea Research Institute of Bioscience and Biotechnology on Aug. 13, 2001 (Accession No: KCTC 10038BP).

The inhibition method of cellular apoptosis of the present invention is hereinafter described in detail.

The cellular pathway leading to apoptosis involves the activation of members of a family of protease, namely, caspases. Among the various apoptosis-related caspases, caspase-3 is known as effector caspase, which works at the final stage of caspase activation.

Cytotoxic materials induce cellular apoptosis in a variety of manners according to type. Since such variously induced apoptosis eventually induces the activation of effector caspase, like caspase-3, the various types of apoptosis signals are gathered by the activation of one or two caspases. In addition, it is known that the caspase-3 has a broad range of intracellular protein substrates.

Accordingly, in the preferred embodiment of the present invention, the present inventors induced the expression of antisense RNA of caspase-3 to inhibit cellular apoptosis. When the expression vector containing the 5' region of antisense nucleotide against caspase-3 is introduced into CHO cells and is expressed, the cellular apoptosis can be inhibited. The expressed antisense RNA restrains translation process during which mRNA information is transferred to peptides by ribosome by combining specifically with sense mRNA sequence which is coding caspase-3, or suppresses the expression of caspase-3 by making mRNA decomposed by antisense-sense RNA double helix structure-specific RNase. In the preferred embodiment of the present invention, recombinant CHO cells producing a humanized antibody against the S-surface antigen of hepatitis B virus were used. The NaBu-induced apoptosis of the recombinant CHO cells was inhibited by introducing the expression vector, which can induce the expression of antisense RNA of caspase-3 into the cells.

EXAMPLES

Practical and presently preferred embodiments of the present invention are illustrative as shown in the following Examples. It will be appreciated, however, that those skilled in the art, on consideration of this disclosure, may make modifications and improvements within the spirit and scope of the present invention.

Example 1

Construction of Expression Vector (ASCASP3-200) Expressing Antisense RNA of Caspase-3

The present inventors constructed the expression vector ASCASP3-200 expressing antisense RNA of caspase-3 as follows. Particularly, the cDNA pool was prepared from mRNAs of CHO cells (DUKX-B11, ATCC CRL-9096) using a Marrathon™ cDNA amplification kit (manufactured by Clontech of Palo Alto, Calif.). The full-length caspase-3 cDNA fragment was amplified from cDNA templates (manufactured by Perkin Elmer) by polymerase chain reaction using two primers, i.e., casp3L (SEQ. ID No. 2) and casp3R (SEQ. ID No. 3). The primer sequences were derived from caspase-3 sequence of human Jurkat T lymphocytes reported previously (Fernandes-Alnemri, et al., 1994, *J. Biol. Chem.*, 269, 30761–30764). The casp3L primer included XbaI restriction enzyme site and 5' start codon. The casp3R primer included BamHI restriction enzyme site and 3' stop codon. The full-length caspase-3 cDNA fragment was inserted into the multi-cloning site of pBluescript II SK(−) cloning vector (obtained from Stratagene of La Jolla, Calif.), yielding pBlue-casp3. The inserted full-length caspase-3 cDNA of CHO cell was sequenced using automated DNA sequencer (ABI prism model 377 by Perkin-Elmer of Poster City, Calif.). The partial fragment containing 5' 200 bp of caspase-3 cDNA was amplified using two primers, i.e., casp3L and casp3R200 (SEQ. ID No. 4). The casp3R200 primer included EcoRI restriction enzyme site and caspase-3 cDNA internal region, which is approximately 200 bp apart from the 5' start codon. In addition, partial cDNA fragment containing about 200 bp of 3' region was amplified by PCR with primers of casp3R and casp3L200 (SEQ. ID No. 5).

The amplified partial fragment of caspase-3 cDNA was inserted, in inverted orientation, into the site between XbaI and EcoRI of mammalian expression vector, pcDNA3.1-zeo(+) (manufactured by InVitrogen of Carlsbad, Calif.), yielding ASCASP3-200. In addition, ASCASP3-200R was also constructed by inserting partial cDNA fragment of 3' region into pcDNA3.1-zeo(+) vector.

The present inventors deposited the above expression vector, ASCASP3-200, at the Korean Collection for Type Cultures, Korea Research Institute of Bioscience and Biotechnology on Aug. 13, 2001 (Accession No. KCTC 10038BP).

Experimental Example 1

Inhibition of Cellular Apoptosis

<1-1> Selection of Caspase-3 Expression-Suppressed CHO Cell Clones

Figure 2:
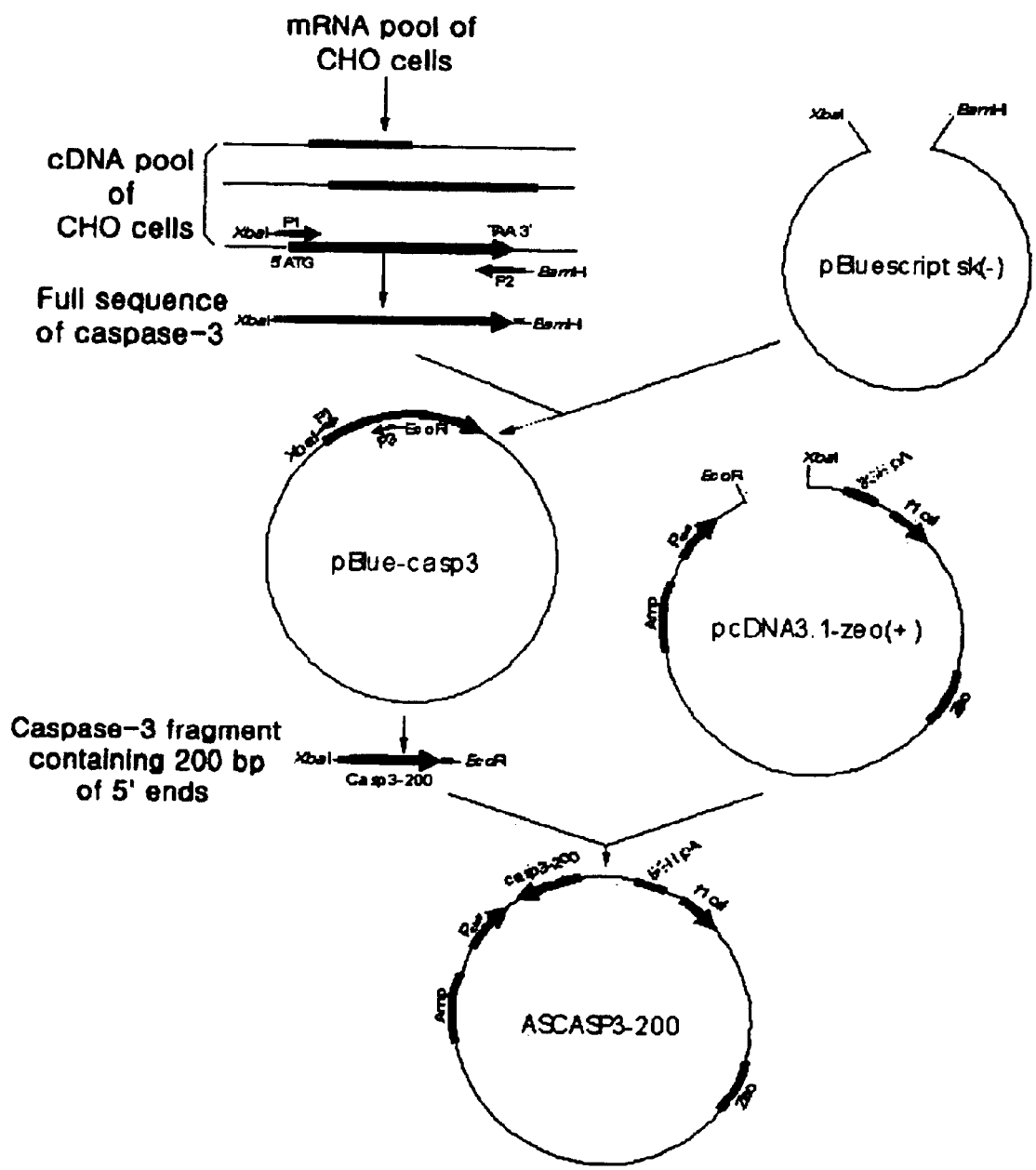
FIG. 2 is a schematic diagram showing the structure of an expression vector ASCASP3-200 designed to express antisense RNA against caspase-3 in recombinant CHO cells producing humanized antibody specific to the S-surface antigen of hepatitis B virus.

Dihydrofolate reductase (dhfr) negative CHO cells (DUKX-B11, ATCC CRL 9096) were maintained in a DMEM/F12 medium (Gibco) supplemented with 10%(V/V) fetal bovine serum (Gibco), 1% hypoxanthine/thymidine (Gibco). The cells were plated in a 60 mm culture dish at densities of $1 \times 10^5$ cells/ml and cultured for 24 hours. Then, humanized antibody expression vector (pKC-dhfr-HC-hus, FIG. 1) was inserted into the cells using liposome. After 48 hours, antibiotics-resistant cells were selected in an alpha-minimum essential medium (Gibco) containing 550 μg/ml of G418 and 10% (V/V) dialyzed fetal bovine serum for two to three weeks. The selected cells were treated with 20 nM, 80 nM, and 320 nM of methotrexate (manufactured by Sigma Chemical Co. of St. Louis Mo.) to enhance antibody productivity. Of the group treated with 320 nM of methotrexate, cells showing the highest antibody productivity were obtained and designated "SH2-0.32." SH2-0.32 cells were transfected with ASCASP3-200 (FIG. 2) using liposome. Drug selection was performed for two weeks by seeding $10^4$ cells/well in 96-well tissue culture plates (manufactured by Nunc of Roskilde, Denmark) containing 200 μl of an alpha-minimum essential medium (Gibco) supplemented with 10% dialyzed fetal bovine serum (Gibco), 500 μg/ml of zeocin (manufactured by Invitrogen), and 0.32 μM of methotrexate (manufactured by Sigma Chemical Co. of St. Louis, Mo.). From this, thirty antibiotics (zeocin)-resistant clones were obtained. To screen the stable clones expressing a reduced level of caspase-3, the antibiotics-resistant clones were assayed by Western blotting against mRNA of caspase-3.

Figure 3:
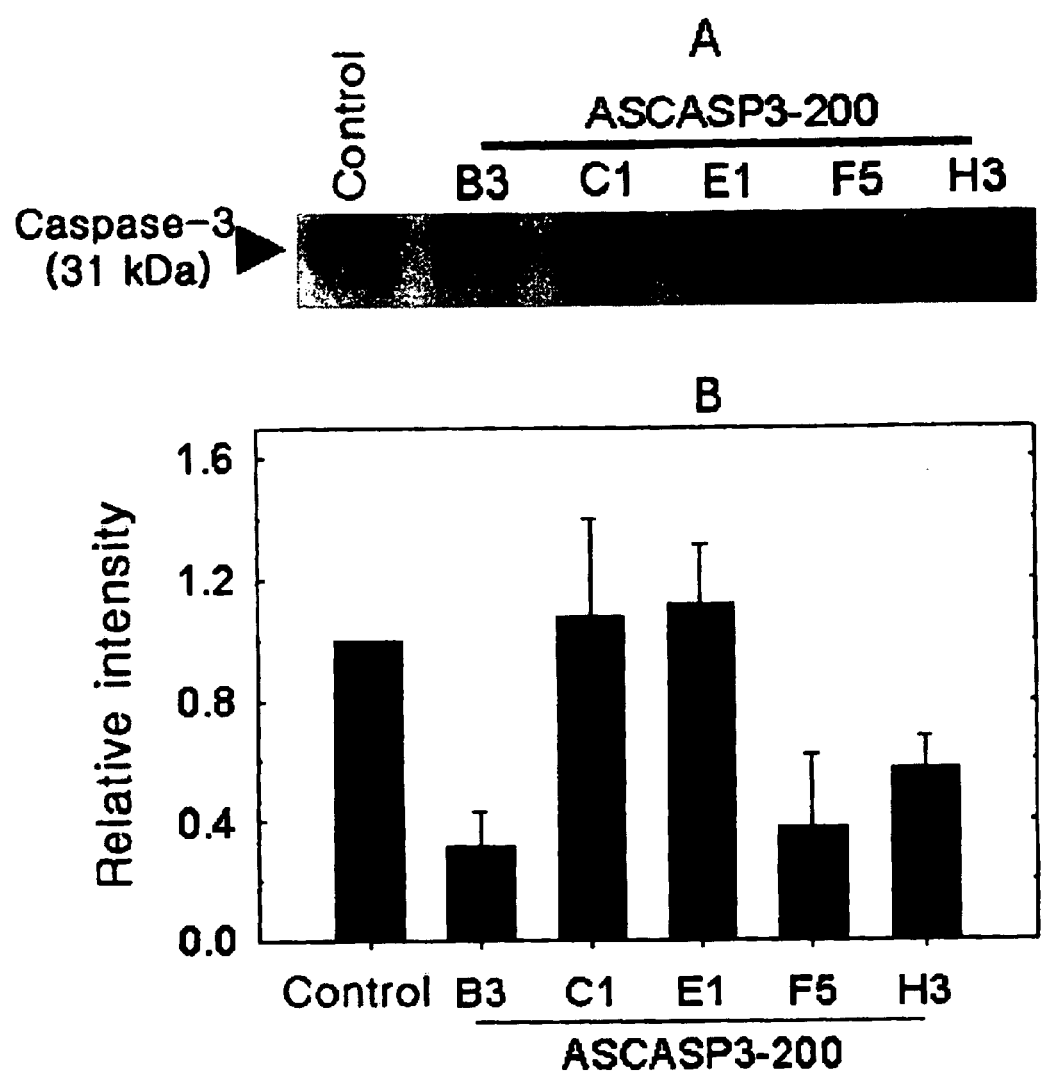
FIGS. 3A and 3B are electrophoresis photographs each showing the result of Western blotting, to screen stable clones expressing a reduced level of caspase-3.

FIGS. 3A and 3B are electrophoresis photographs each showing the result of Western blotting to screen stable clones expressing a reduced level of caspase-3, with FIG. 3 showing a band intensity quantified using computerized software. Here, each of B3, C1, E1, F5, and H3 are cell clones containing the expression vector ASCASP3-200, with the B3 cells showing a suppressed caspase-3 expression, the C1 cells showing no suppressed caspase-3 expression, the E1 cells showing no suppressed caspase-3 expression, the F5 cells showing a reduced caspase-3 expression, and the H3 cells showing a reduced caspase-3 expression.

As can be seen from FIGS. 3A and 3B, a cell clone showed significantly reduced level of caspase-3 expression was selected and designated "ASCASP3-200 B3" (hereinafter, simply "B3"). The B3 cells were used in further experiments. At this time, cells constructed by transfecting SH2-0.32 cells with null pcDNA3.1-zeo(+) without antisense caspase-3 fragment were used as a control. In addition, cells constructed by transfecting SH2-0.32 cells with ASCASP3-200R containing 3' partial fragment of antisense RNA were used as a comparative group.

<1-2> Inhibition of Cellular Apoptosis by Expressing Antisense RNA of Caspase-3

The present inventors confirmed whether the expression of antisense RNA of caspase-3 could inhibit the NaBu-induced apoptosis. Particularly, control cells and B3 cells obtained in Example <1-1> were seeded at a concentration of $4 \times 10^4$ cells/ml in 6-well culture plates containing 5 ml of an alpha-minimum essential medium supplemented with 5% dialyzed fetal bovine serum and 0.32 μM of methotrexate. After three days of cultivation, the spent medium was replaced with fresh medium containing 0–5 mM of sodium butyrate. Cells were harvested periodically. Viable cells were distinguished from dead cells using the trypan blue dye exclusion method to determine cell viability. In addition, secreted humanized antibody concentration was measured by enzyme-linked immunosorbent assay (ELISA).

Figure 4:
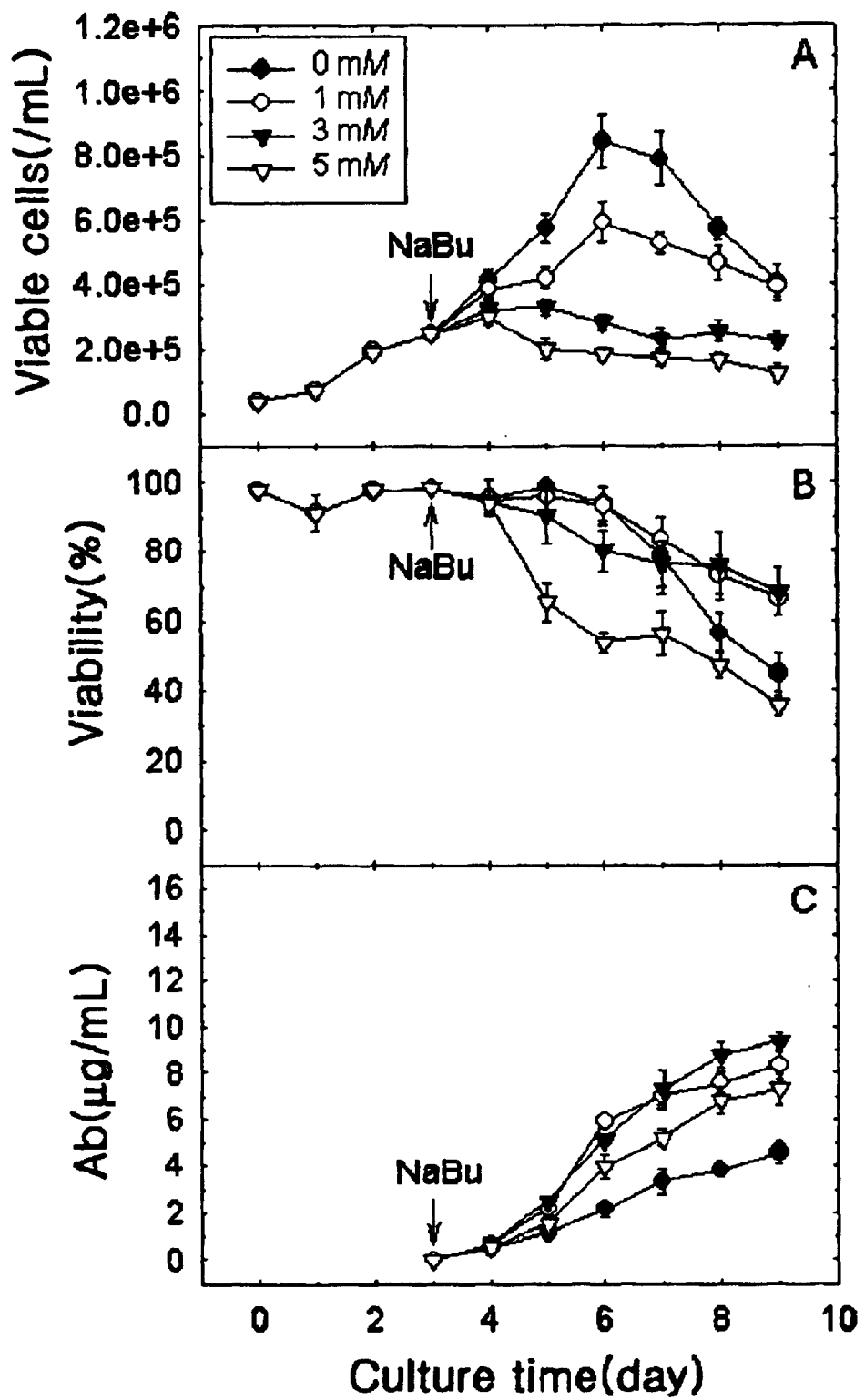
FIGS. 4A, 4B, and 4C are graphs showing the cell growth, viability, and the extent of antibody expression, respectively, after treating a batch culture of control cells with various concentrations of sodium butyrate.
Figure 5:
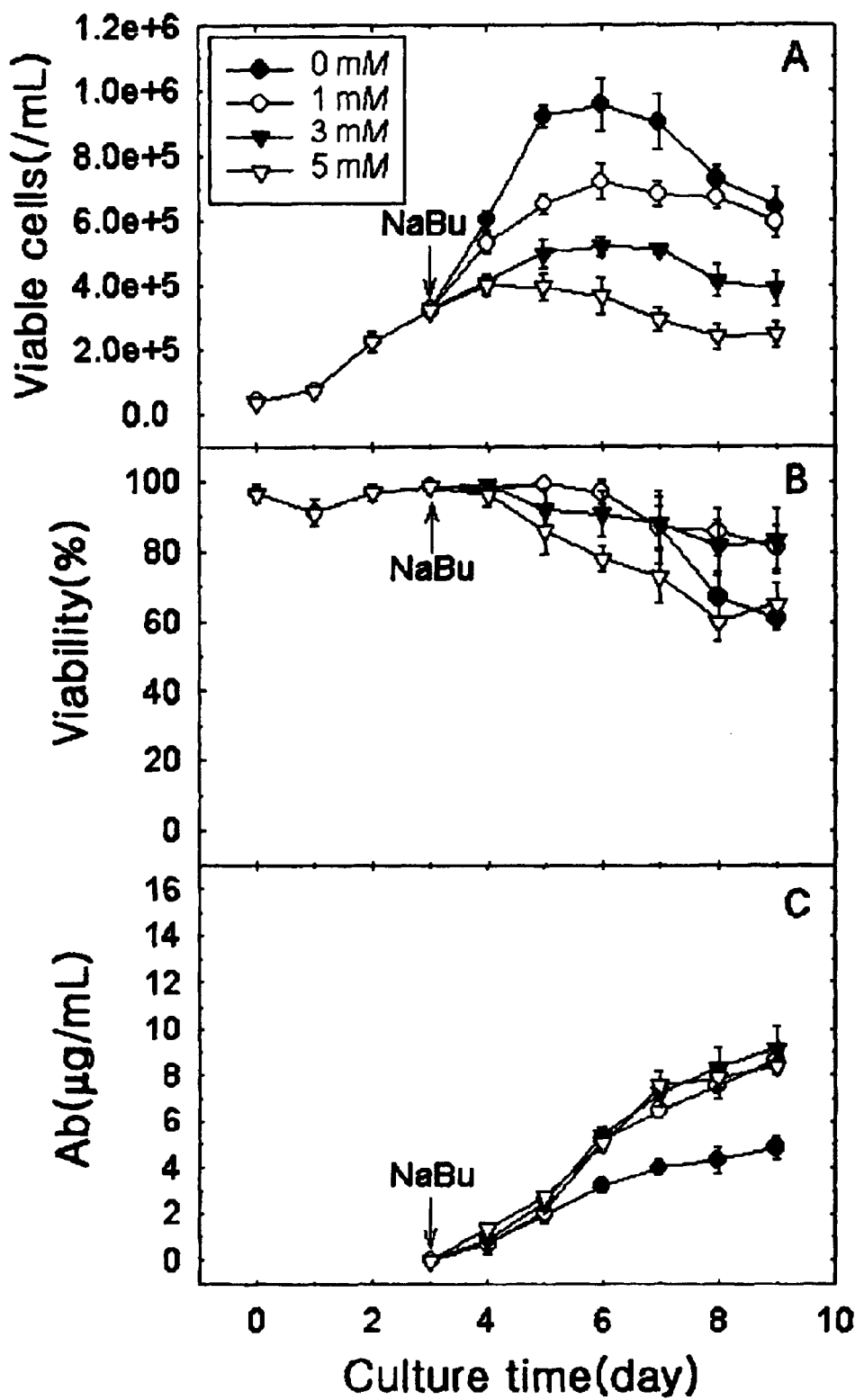
FIGS. 5A, 5B, and 5C are graphs showing the cell growth, viability, and the extent of antibody expression, respectively, after treating a batch culture of B3 cells with various concentrations of sodium butyrate.
Figure 6:
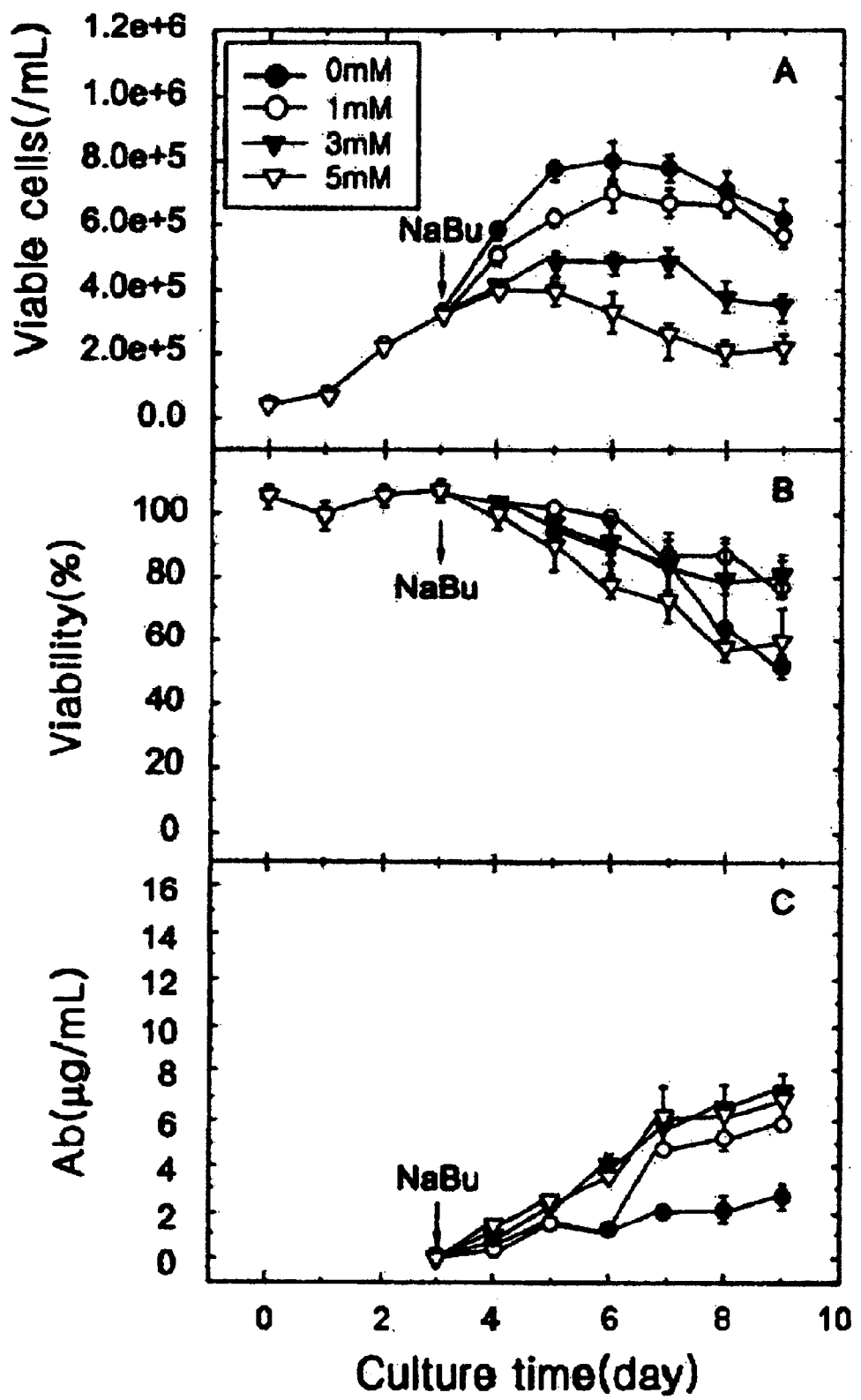
FIGS. 6A, 6B, and 6C are graphs showing the cell growth, viability, and the extent of antibody expression, respectively, after treating a batch culture of comparative cells with various concentrations of sodium butyrate.

As a result, it was confirmed that the cytotoxic effect of sodium butyrate on the cell growth was dose-dependent. Especially, cellular apoptosis was induced in the presence of 5 mM of sodium butyrate (FIGS. 4A and 5A). From 24 hours after the treatment with 5 mM of sodium butyrate, the viability of control cells began to decrease significantly and was under 50% three days later (FIG. 4B). In the case of B3 cells, sodium butyrate also decreased the cell growth rate, as in the control group, but there was a significant difference when treated with 5 mM of sodium butyrate. That is, the drastic decrease of viability was not observed in B3 cells even after 24 hours of the treatment (FIG. 5B). In case of comparative group, the viability began to decrease from 24 hours after the treatment with 5 mM of sodium butyrate (FIG. 6B). This result came from a caspase-3 activity of B3 cells that was lower than that of the control or comparative group, by suppressing the expression of caspase-3 by antisense RNA of caspase-3. Nevertheless, the final antibody concentration, obtained in B3 cells subjected to the treatment with 5 mM of sodium butyrate, was similar to that obtained in the control or comparative cells (FIGS. 4C, 5C and 6C) despite its improved cell viability by the inhibition of caspase-3 activation. This similarity is because the ATP energy synthesis, necessary for the protein synthesis metabolism of cells, was inhibited by the mitochondrial membrane depolarization caused by the disruption of mitochondrial membrane by sodium butyrate.

Experimental Example 2

Determination of LDH Activity in Culture Medium

Although the improved cell viability due to the resistance against the cytotoxicity of sodium butyrate acquired by efficient expression of antisense RNA of caspase-3 does not increase the final foreign protein concentration, it may improve the integrity of the foreign protein. The integrity of protein product is influenced by the degree of cell lysis because some proteolytic enzymes and glycosidases released from the cellular membrane ruptured-dead cells influence the molecular integrity of the product (Goldman, et al., 1997, *Cytotechnology*, 23, 103–111; Hansen, et al., 1997, *Cytotechnology*, 24, 227–234; Teige, et al., 1994, *J. Biotechnol.*, 34, 101–105). The amount of lysed cells can be determined by measuring the amount of lactate dehydrogenase (LDH) released into the culture supernatant (Cruz, et al., 2000, *Biotechnol. Lett.*, 22, 677–682). Thus, to determine the degree of cell lysis, the LDH activity in culture supernatant was measured daily after treatment with 5 mM of sodium butyrate.

Figure 7:
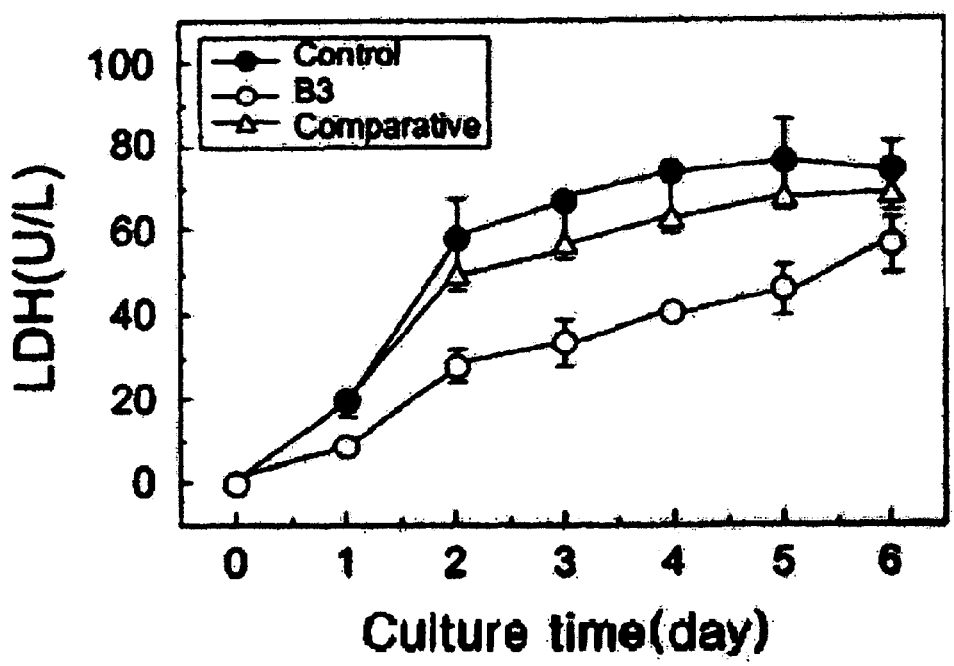
FIG. 7 is a graph showing the time-course changes in extracellular LDH activity in a culture medium after treatment with 5 mM of sodium butyrate.

As a result, the LDH activity increased rapidly in the control cells for the first two days after the addition of sodium butyrate and thereafter increased gradually to the end of cultivation. The LDH activity also increased in the B3 cells, but much more slowly than that of the control or comparative cells, indicating that the cellular membrane integrity of B3 cells was improved by inhibition of apoptotic cell death (FIG. 7). Therefore, inhibition of caspase-3 by expressing 5' region of antisense RNA of caspase-3 contributes to enhance the integrity of produced foreign protein but not productivity of the protein. The antisense RNA of the present invention can be effectively used to produce protease-sensitive foreign proteins such as interferon-gamma, factor VIII, thrombopoietin, and erythropoietin.

As shown above, apoptosis can be inhibited by suppressing the activation of caspase-3, which is related to the apoptosis. Further, the integrity of target protein produced in the recombinant cells can be enhanced.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An expression vector ASCASP3-200 containing the antisense nucleotide sequence as shown in SEQ ID NO: 1 and expressing antisense RNA of caspase-3 (Accession No: KCTC 10038BP).

2. An inhibition method of apoptosis of recombinant cells, comprising steps of suppressing the expression of caspase-3 by introducing the expression vector of claim 1 into the recombinant cells; and expressing antisense RNA of caspase-3.

3. The inhibition method as set forth in claim 2, wherein a Chinese hamster ovary (CHO) cell line is used as the recombinant cells.

4. A composition for the inhibition of apoptosis of recombinant cells, comprising the expression vector of claim 1.

5. An inhibition method of apoptosis of recombinant cells, comprising steps of: suppressing the expression of caspase-3 by introducing the antisense nucleotide sequence as shown in SEQ. ID No. 1 into the recombinant cells; and expressing antisense RNA of caspase-3.

6. The inhibition method as set forth in claim 5, wherein a Chinese hamster ovary (CHO) cell line is used as the recombinant calls.

* * * * *